United States Patent
Wang et al.

(10) Patent No.: US 9,918,786 B2
(45) Date of Patent: Mar. 20, 2018

(54) SPINAL DISK HERNIATION REPOSITIONING AND RADIOFREQUENCY ABLATION (RFA) DEVICE AND METHOD FOR TREATING VERTEBRAL DISC HERNIATION

(71) Applicants: Hongkui Wang, Beijing (CN); Jinsheng Wang, Shenyang (CN)

(72) Inventors: Hongkui Wang, Beijing (CN); Jinsheng Wang, Shenyang (CN)

( * ) Notice: Subject to any disclaimer, the term of this patent is extended or adjusted under 35 U.S.C. 154(b) by 135 days.

(21) Appl. No.: 14/046,991

(22) Filed: Oct. 6, 2013

(65) Prior Publication Data

US 2015/0100052 A1  Apr. 9, 2015

(51) Int. Cl.
| | |
|---|---|
| A61B 18/18 | (2006.01) |
| A61B 18/14 | (2006.01) |
| A61B 18/00 | (2006.01) |
| A61B 17/32 | (2006.01) |
| A61B 18/06 | (2006.01) |
| A61B 18/08 | (2006.01) |

(52) U.S. Cl.
CPC .. *A61B 18/1482* (2013.01); *A61B 17/320068* (2013.01); *A61B 18/06* (2013.01); *A61B 18/08* (2013.01); *A61B 18/1477* (2013.01); *A61B 18/1815* (2013.01); *A61B 2018/00339* (2013.01); *A61B 2018/00577* (2013.01); *A61B 2018/00791* (2013.01); *A61B 2018/00821* (2013.01); *A61B 2018/1807* (2013.01)

(58) Field of Classification Search
CPC .. A61B 2018/00339; A61B 2018/1475; A61B 18/1482; A61B 17/320068; A61B 18/06; A61B 18/08; A61B 18/1477; A61B 18/1815; A61B 2018/00577; A61B 2018/00791; A61B 2018/00821; A61B 2018/1807
See application file for complete search history.

(56) References Cited

U.S. PATENT DOCUMENTS

| | | | |
|---|---|---|---|
| 5,433,739 A * | 7/1995 | Sluijter et al. | 607/99 |
| 5,730,127 A * | 3/1998 | Avitall | 600/374 |
| 5,921,924 A * | 7/1999 | Avitall | A61B 5/0422 600/373 |
| 5,976,105 A | 11/1999 | Marcove | |
| 6,053,937 A * | 4/2000 | Edwards et al. | 607/104 |
| 6,264,651 B1 | 7/2001 | Underwood et al. | |
| 6,277,112 B1 | 8/2001 | Underwood et al. | |
| 6,283,961 B1 | 9/2001 | Underwood et al. | |
| 6,419,673 B1 * | 7/2002 | Edwards et al. | 606/41 |

(Continued)

*Primary Examiner* — Joseph Stoklosa
*Assistant Examiner* — Tigist Demie
(74) *Attorney, Agent, or Firm* — Peter B. Scull; Hamilton, DeSanctis & Cha LLP

(57) ABSTRACT

Devices, components, apparatus, and/or methods for using and making a combination spinal disk herniation repositioning and radiofrequency apparatus (RFA) or device that uses one or more repositioning probes and one or more needles/electrodes, wherein the device's probe repositions, and the electrode or needle treats or ablates, an injured, torn, herniated, or displaced vertebral disc propulus and/or nucleus, and wherein one or more side probes or needles are used to reposition or treat the spinal disk herniation, optionally followed by medicine/ozone therapy of the disc being treated.

2 Claims, 8 Drawing Sheets

(56) References Cited

U.S. PATENT DOCUMENTS

| | | |
|---|---|---|
| 6,500,173 B2 | 12/2002 | Underwood et al. |
| 6,540,741 B1 | 4/2003 | Underwood et al. |
| 6,620,155 B2 | 9/2003 | Underwood et al. |
| 6,712,811 B2 | 3/2004 | Underwood et al. |
| 6,749,605 B2 | 6/2004 | Ashley et al. |
| 7,267,683 B2 | 9/2007 | Sharkey et al. |
| 7,270,658 B2 | 9/2007 | Woloszko et al. |
| 7,282,061 B2 | 10/2007 | Sharkey et al. |
| 7,309,336 B2 | 12/2007 | Ashley et al. |
| 7,400,930 B2 | 7/2008 | Sharkey et al. |
| 8,226,697 B2 | 7/2012 | Sharkey et al. |
| 9,138,530 B2 * | 9/2015 | Clair ................. A61M 25/0084 |
| 9,186,207 B2 * | 11/2015 | Elmouelhi ......... A61B 18/1477 |
| 2002/0065541 A1 * | 5/2002 | Fredricks et al. .............. 607/96 |
| 2002/0115992 A1 * | 8/2002 | Utley et al. ..................... 606/41 |
| 2005/0059964 A1 * | 3/2005 | Fitz ................................ 606/41 |
| 2005/0273093 A1 | 12/2005 | Patel et al. |
| 2007/0219546 A1 * | 9/2007 | Mody et al. .................... 606/27 |
| 2008/0103504 A1 * | 5/2008 | Schmitz et al. ................ 606/79 |
| 2010/0049031 A1 * | 2/2010 | Fruland et al. ............... 600/411 |
| 2010/0185161 A1 * | 7/2010 | Pellegrino et al. ........... 604/272 |
| 2012/0065634 A1 * | 3/2012 | Lee et al. ........................ 606/41 |
| 2012/0089141 A1 | 4/2012 | Lee et al. |

\* cited by examiner

SPINAL DISK HERNIATION REPOSITIONING AND RADIOFREQUENCY ABLATION (RFA) DEVICE AND METHOD FOR TREATING VERTEBRAL DISC HERNIATION

FIELD OF THE INVENTION

The invention relates to a combination spinal disk herniation repositioning and radiofrequency ablation device, apparatus, system, and method for treating spinal disc herniation.

BACKGROUND

Spinal Disk Herniation is a common disease wherein it has been reported that many patients who suffered from back or leg pain are diagnosed with spinal disk herniation. In recent years, the number of patients have increased significantly throughout the world. It is a disease that has affected almost all age groups, and thus it is important to develop new minimally invasive procedures that help treating millions of patients. The existing methods of treating Spinal Disk Herniation include, e.g., (a) Massage/Physical Therapy wherein the effectiveness of this method is often questioned and is not very reliable; (b) Surgeries, wherein while this is a proven procedure, its drawbacks include the obvious: high cost and risks as known; and (c) Existing minimally invasive procedures, including ozone injection, radiofrequency ablation, and laser disk decompression, which are typically less invasive and often carry less risks, resulting in quicker recovery, and thus can be favored by patients. However, such minimally invasive procedures are often not as effective as traditional surgeries. For both patients and clinical professionals, there is a need to provide a procedure that is not only minimum invasive, but also clinically effective.

SUMMARY

Accordingly, the invention provides devices and methods to treat disc abnormalities such as disc degeneration or herniation without major surgical intervention or substantial destruction to the disc. The invention further optionally provides devices and methods for the treatment of disc abnormalities via controlled high-energy input available through radio frequency energy, optionally to the nucleus pulposus at the posterior, posterior lateral and the posterior medial regions of the inner wall of the annulus fibrosis; optionally further administering materials to, or remove materials from, a precise, selected location within the disc, optionally to the location of the annular fissure. The invention also optionally provides thermal energy into collagen in the area of the fissure to strengthen the annulus, optionally to fuse collagen to the sides of the fissure, optionally at the posterior, posterior lateral and the posterior medial regions of the inner wall of the annulus fibrosus.

The invention optionally provides or more or devices, components, apparatus, and/or methods for using and making a combination spinal disk herniation repositioning and radiofrequency apparatus (RFA) or device that uses one or more repositioning probes and one or more needles/electrodes, wherein the device's probe repositions, and the electrode or needle treats or ablates, an injured, torn, herniated, or displaced vertebral disc propulus and/or nucleus, and wherein one or more side probes or needles are used to reposition or treat the spinal disk herniation, optionally followed by medicine/ozone therapy of the disc being treated.

Non limiting embodiments of the invention can include one or more of devices, components, apparatus, and/or methods for using and making a combination spinal disk herniation repositioning and radiofrequency ablation (RFA) apparatus or device that uses two needles/electrodes, wherein the electrode's probe treats or ablates an injured, torn, herniated, or displaced vertebral disc propulus and/or nucleus, and optionally wherein one or more side needles/electrodes and/or probes are used to reposition the spinal disk herniation, followed by RFA treatment of the injured, torn, herniated, and/or displaced vertebral disc, optionally further comprising medicine/ozone therapy of the disc being treated.

Such a nonlimiting embodiment of the invention can provide minimally invasive procedure(s) with comparable clinical effect as compared to known or traditional surgeries. Such advantages can include one or more of, but not limited to: reduced or avoided need for more invasive surgeries; less pain for the patients; and/or quicker recovery, hospital stay, and/or follow up or treatment.

Non limiting optional embodiments of the invention can also optionally provide a new way to treat spinal disk herniation through a radiofrequency ablation electrode with spinal disk herniation repositioning features in the same device or shaft, e.g., using concentric shafts which can also provide administration or removal of compounds, fluids, or agents.

The method optionally overcomes the shortcomings of traditional minimally invasive techniques, allowing patients to have immediate recovery after the procedure. Under the guidance of imaging devices (e.g. CT, CAT, MRI, etc.), physicians or medical professionals would optionally use the electrode's probe to puncture the body. After the needle reaches the injured disk, the physician can optionally deploy the side needle in order to reposition the spinal disk herniation or other anatomical structures to expose or separate the damaged or diseased tissue in preparation for ablation. Later the physician can optionally further perform radiofrequency ablation treatment and/or medicine/ozone therapy with the device.

Non-limiting optional embodiments of the invention can use mechanical or other forces to separate the diseased tissue from the trapped spinal disk herniation tissues: termed "repositioning". When those tissues are pushed back into their original positions, patients' back pain will be greatly relieved. Later radiofrequency ablation procedure will be performed in order to reduce the size of the diseased tissues, further reducing the chance of oppressing the nerves by those tissues. With the same radiofrequency ablation electrode, physician could also inject ozone or collagenase later to deal with infections and to further reduce pains. This comprehensive approach of treatment can be as effective as, or an improvement over, surgeries, but also offers the benefits of avoiding surgeries (quicker recovery, less pain, less damage to the body, etc.).

Another object of the invention is to provide a minimally invasive method and apparatus for treating morphological abnormalities of discs at selected locations within the disc via radio frequency ablation electrode(s) in combination in a single device with a second needle to reposition, retract or move adjacent or nearby diseased tissue.

Another object of the invention is to provide a device which has a distal end that is inserted into the disc and accesses the posterior, posterior lateral and the posterior medial regions of the inner wall of the annulus fibrosis for application of RF energy at such location in combination in a single device with a second needle to reposition, retract or move adjacent or nearby diseased tissue Another object of the invention is to provide an apparatus which is advanceable and navigable at the inner wall of the annulus fibrosus to provide localized heating at the site of the annular fissure in combination in a single device with a second needle to reposition, retract or move adjacent or nearby diseased tissue.

Another object of the invention include providing apparatus and methods for diagnosing an abnormality and/or adding or removing a material at a preselected location of a disc via a functional element in combination in a single device with a second needle to reposition, retract or move adjacent or nearby diseased tissue.

Another object of the invention is to provide a device which has a distal end that is inserted into the disc and accesses the posterior, posterior lateral and the posterior medial regions of the inner wall of the annulus fibrosus in order to repair or shrink an annular fissure at such a location in combination in a single device with a second needle to reposition, retract or move adjacent or nearby diseased tissue.

Another object of the invention is to provide a non-destructive method and apparatus for treating morphologic abnormalities of discs in combination in a single device with a second needle to reposition, retract or move adjacent or nearby diseased tissue.

Another object of the invention is to provide a method and apparatus to treat degenerative intervertebral discs by delivering thermal energy to denervate selective nerves embedded in the walls of the disc in combination in a single device with a second needle to reposition, retract or move adjacent or nearby diseased tissue.

Another objective of the invention is to provide a method and apparatus to treatment of degenerative intervertebral discs by delivering thermal energy to cauterize granulation tissue that is ingrown in the wall of the disc in combination in a single device with a second needle to reposition, retract or move adjacent or nearby diseased tissue.

Another object of the invention is to provide a method and apparatus to treat degenerative intervertebral discs by delivering thermal energy to break down selected enzyme systems and neurotransmitters that generate pain within the disc in combination in a single device with a second needle to reposition, retract or move adjacent or nearby diseased tissue.

Another object of the invention is to provide a method and apparatus to treat degenerative intervertebral discs by shrinking a selected amount of collagen in the annulus fibrosis of the disc and remove a redundancy in the disc roll in combination in a single device with a second needle to reposition, retract or move adjacent or nearby diseased tissue.

Another object of the invention is to provide a method and apparatus to treat degenerative intervertebral discs by delivering thermal energy to at least a portion of the nucleus pulposus to reduce water content of the nucleus pulposus and shrink the nucleus pulposus without creating a contained herniated disc in combination in a single device with a second needle to reposition, retract or move adjacent or nearby diseased tissue.

Another object of the invention is to provide a method and apparatus to treat degenerative intervertebral discs by supplying sufficient thermal energy to shrink the nucleus pulposus and tighten the disc in combination in a single device with a second needle to reposition, retract or move adjacent or nearby diseased tissue.

Another object of the invention is to provide an apparatus to treat degenerative intervertebral discs which is advanceable and navigational adjacent to an inner wall of the annulus fibrosis in combination in a single device with a second needle to reposition, retract or move adjacent or nearby diseased tissue.

Another object of the invention is to provide a thermal energy delivery device which has a distal end that is inserted into the nucleus pulposus and accesses the posterior, posterior lateral and the posterior central regions of the inner wall of the nucleus fibrosis in combination in a single device with a second needle to reposition, retract or move adjacent or nearby diseased tissue.

The invention optionally provides in non-limiting embodiments an intervertebral disc apparatus that includes an introducer with an introducer lumen and a catheter. The catheter is at least partially positioned in the introducer lumen and includes a probe section including a nerve repositioner and an energy delivery device coupled to the intradiscal section. The intradiscal section is configured to be advanceable through a nucleus pulposus of the intervertebral disc and positionable adjacent to a selected site of an inner wall of an annulus fibrosis. The energy delivery device is configured to deliver sufficient energy to heat at least a portion of the intervertebral disc without substantially removing intervertebral disc material positioned adjacent to the energy delivery device.

The invention also includes providing in non limiting optional embodiments an externally guidable intervertebral disc apparatus for manipulation of disc tissue present at a preselected location of an intervertebral disc, the disc having a nucleus pulposus, an annulus fibrosis, and an inner wall of the annulus fibrosis, the nucleus pulposus having a first diameter and a disc playing between opposing sections of the inner wall, proximity to the nucleus being provided by an introducer comprising an internal introducer lumen with an opening at a terminus of the introducer, comprising a catheter having a distal end and a proximal end having a longitudinal access, the catheter being adapted to slidably advance through the introducer lumen, the catheter having an intradiscal section at the distal end of the catheter, the intradiscal section being extendable through the opening of the introducer and having sufficient rigidity to be advanceable through the nucleus pulposus of the disc and around the inner wall of the annulus fibrosis under a force applied longitudinally to the proximal end and having insufficient penetration ability to be advanceable through the inner wall of the annulus fibrosis under the force; and a heating element located at the intradiscal section selected from the group consisting of RF heating elements, resistive heating elements, chemical heating elements, and ultrasound heating elements, in combination with at least one spinal disk herniation repositioning element and further comprising in combination in the same distal end a spinal disk herniation repositioning element, needle, tip, or the like.

A non limiting optional embodiment of the invention is based on a catheter for delivering energy to a surgical site in combination with the same device and concentric positioned spinal disk herniation repositioning element, needle or tip that is moveable longitudinally within the catheter, which can be stiff and made of at least one of metal, plastic, polymer or fiber. The catheter optionally includes at a proximal end a handle and at a distal end a probe, shaft and/or tip. The catheter optionally includes at least one energy delivery device and an activation element and a spinal disk herniation repositioning element. The at least one energy device is located at the distal end of the catheter to deliver energy to portions of the surgical site in combination with a spinal disk herniation repositioning element. The activation element is optionally located at the distal end of the catheter, to transition the probe from a linear to a multi-dimensional shape, within the surgical site. In another optional embodiment of the invention, the catheter includes a substrate and a heating element. The substrate is located at the distal end of the catheter.

In another optional embodiment of the invention the catheter includes a first probe section, at least one energy delivery element, a tip and a spinal disk herniation repositioning element or blade. The first probe section optionally defines along a length thereof at least one first lumen. The at least one energy delivery element is optionally located at the distal end of the catheter to deliver energy to portions of the intervertebral disc while also repositioning spinal disk herniation as needed. The tip is optionally coupled to the first probe section at a terminus thereof. The tip optionally defines on an exterior face a second lumen substantially concentric with said first lumen. The spinal disk herniation repositioning element or blade is optionally positioned within the first lumen and is extensible from a first position within said first probe section, to a second position extending through the second lumen and beyond the tip, to reposition spinal disk herniation and/or cut selected portions within the intervertebral disc.

In another optional embodiment of the invention a catheter optionally includes an energy delivery element, a material transfer element, and at least one interface on the handle thereof. The energy delivery element is optionally located at the distal end of the catheter to deliver energy to portions of the intervertebral disc. The optionally material transfer element is optionally located at the distal end of the catheter to transfer material to and from the intervertebral disc. The at least one interface on the handle optionally couples the energy delivery element and the spinal disk herniation repositioning and/or material transfer element to external devices for energy and spinal disk herniation repositioning and/or material transfer to and from the intervertebral disc.

In still another optional embodiment of the invention a method for deploying a probe portion of a catheter in a multi-dimensional shape within a surgical site is optionally disclosed. The method optionally includes the steps of: configuring the probe of the catheter in a substantially linear configuration; applying a sufficient force to advance the probe of the catheter through the nucleus pulposus, which force is insufficient to puncture the annulus fibrosus; deploying the probe in a substantially arcuate configuration within the inner wall of the annulus fibrosus, and repositioning spinal disk herniation and delivering energy from the same probe in an optional concentric configuration to portions of the intervertebral disc.

DESCRIPTION

Figure 1:
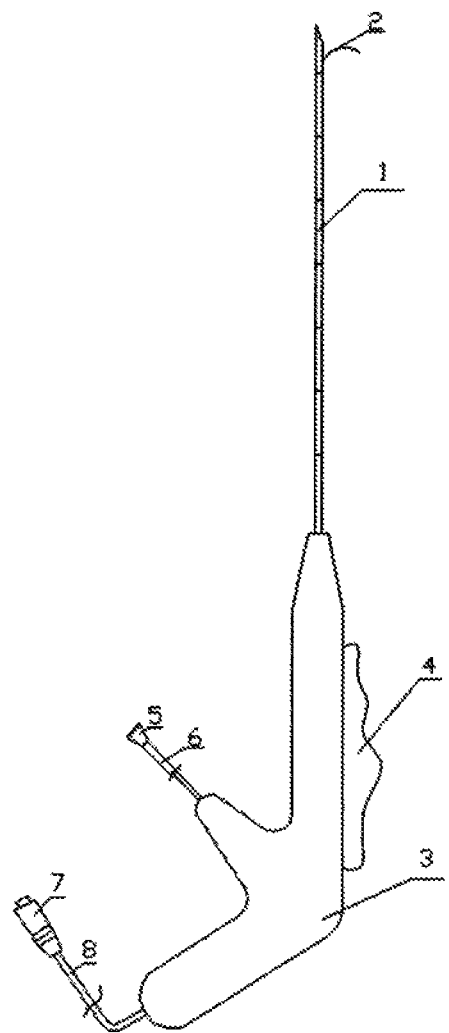
FIG. 1 is an exterior view of a schematic picture of a non-limiting example of a device of the invention.

The present invention provides in optional non-limiting embodiments a method and apparatus for treating intervertebral disc disorders by the application of controlled RF or heating in combination with spinal disk herniation repositioning in the same device or shaft to a localized region of an intervertebral disc. Such related disorders can include but are not limited to (i) degenerative discs which have tears or fissures in the annulus fibrosis, particularly fissures of the annulus fibrosis, which may or may not be accompanied with contained or escaped extrusions, (ii) contained disc herniation with focal protrusions, and/or (iii) bulging discs.

Degenerative discs with tears or fissures can be treated non-destructively, optionally without the significant removal of disc tissue other than torn or damaged or adjacent tissue by limited ablation and spinal disk herniation repositioning to the nucleus pulposus which can optionally change some of the water content, shape, or composition of the nucleus pulposus. Electromagnetic such as RF energy can optionally be delivered to a selected section of the disc in combination with spinal disk herniation repositioning in the same instrument wherein the energy can optionally be provided in an amount which does not create a destructive lesion to the disc. Sufficient electromechanical or RF energy is delivered to the disc to change its biochemical, neurophysiologic and/or biomechanical properties in order to optionally reduce at least one of pain, inflammation, tearing, displacement, swelling, necrosis, nerve impingement, and/or damage. Neurophysiologic modifications can optionally include denervation of nociceptors in a tear or fissure in the annulus fibrosis.

Degenerative intervertebral discs with fissures can optionally be treated by repositioning, cutting, and/or denervating selected or relevant nerves that are optionally embedded in the interior wall of the annulus fibrosis optionally as well as nerves outside of the interior wall including those on the surface of the wall. Electromagnetic or RF energy can optionally be used to cauterize granulation or other tissue which can be pain sensitive areas and formed in the annulus fibrosis wall. Electromagnetic or RF energy can also optionally be used to break down selected enzyme systems or neurotransmitters that generate pain within or related to the disc or nerves passing through the disc. Generally, these enzymes and neurotransmitters can work within a small bandwidth of both pH and temperature.

Electromagnetic such as RF energy is applied to shrink collagen in the annulus fibrosis and/or nucleus pulposus. This reduces the redundancy in the disc roll that is created in a degenerative disc. Delivery of electromagnetic energy to the nucleus pulposus removes some water and permits the nucleus pulposus to withdraw. This reduces a "pushing out"

effect that created a contained herniation. Combinations of shrinking the disc, shrinking of the nucleus pulposus by reducing water content, as well as tightening up the annulus fibrosis wall, in combination with spinal disk herniation repositioning, optionally creates a rejuvenation or repair of the disc and/or reduction in pain or inflammation. Reducing the pressure in the disc and tightening the annulus fibrosis optionally produces a favorable biomechanical effect. Application of electromagnetic energy locally increases the stiffness of the disc.

The annulus fibrosis is comprised primarily of fibrosis-like material and the nucleus pulposus is comprised primarily of an amorphous colloidal gel. The distinction between the annulus fibrosis and the nucleus pulposus becomes more difficult to distinguish when a patient is 30 years old or greater. There is often a transition zone between the annulus fibrosis and the nucleus pulposus made of fibrosis-like material and amorphous colloidal gel. For purposes of this disclosure, the inner wall of the annulus fibrosis includes the young wall comprised primarily of fibrosis-like material as well as the transition zone which includes both fibrous-like material and amorphous colloidal gels (hereinafter collectively referred to as "inner wall of the annulus fibrosis").

In general, an apparatus of the invention is optionally in the form of an externally guidable intervertebral disc apparatus for accessing and manipulating disc tissue present at a selected location of an intervertebral disc having a nucleus pulposus and an annulus fibrosus, the annulus having an inner wall. Optional use of a temperature-controlled energy delivery element, combined with spinal disk herniation positioning element and navigational control of the inventive catheter, provides preferential, localized heating and spinal disk herniation reposition to treat the fissure. For ease of reference to various manipulations and distances described below, the nucleus pulposus can be considered as having a given diameter in a disc plane between opposing sections of the inner wall. This nucleus pulposus diameter measurement allows instrument sizes (and parts of instruments) designed for one size disc to be readily converted to sizes suitable for an instrument designed for a different size of disc.

The operational portion of the apparatus of the invention is optionally brought to a location in or near the disc's fissure using techniques and apparatuses typical of percutaneous interventions as known in the art. For convenience and to indicate that the apparatus of the invention can be used with any insertional apparatus that provides proximity to the disc, including many such insertional apparatuses known in the art, the term "introducer" is used to describe this aid to the method. An introducer has at least one internal introducer lumen with a distal opening at a terminus of the introducer to allow insertion (and manipulation) of the operational parts of the apparatus into (and in) the interior of a disc.

The operational part of the apparatus optionally comprises at least one elongated element referred to as a catheter, various parts of which are located by reference to a distal end and a proximal end at opposite ends of its longitudinal axis. The proximal end is the end closest to the external environment surrounding the body being operated upon (which may still be inside the body in some embodiments if the catheter is attached to a handle insertable into the introducer). The distal end of the catheter is optionally intended to be located inside the disc under conditions of use. The catheter is optionally a traditional medical catheter (i.e., an elongate hollow tube for admission or removal of fluids from an internal body cavity) but is a defined term for the purposes of this specification. "Catheter" has been selected as the operant word to describe this part of the apparatus, as the inventive apparatus is optionally a long, flexible, partly flexible or rotatably, or at least partially stiff or rigid tube which transmits energy, spinal disk herniation repositioning, and/or material from or to a location external to the body to a location internal to the disc being accessed upon, such as optionally a collagen solution, spinal disk herniation repositioning, and./or heat to the annular fissure. Alternatively, material can be transported in the other direction to remove material from the disc, such as removing material by aspiration to decrease pressure which is keeping the fissure open and aggravating the symptoms due to the fissure.

The catheter is optionally adapted to slidably advance through the introducer lumen, the catheter optionally having a probe section at the distal end of the catheter, the probe section being extendible through the distal opening at the terminus of the introducer into the disc and can include an RF needle, electrode or tip and a spinal disk herniation repositioning needle or tip. Although the length of the probe portion can vary with the intended function as explained in detail below or as known in the art, a typical distance of extension is optionally at least one-half the diameter of the nucleus pulposus, preferably in the range of one-half to one and one-half times the circumference of the nucleus.

In order that the functional elements of the catheter (e.g., an electromagnetic probe, such as, an RF electrode or a resistance heater, and a spinal disk herniation repositioning element, e.g., probe, needle or tip) can be readily guided to the desired location within a disc, the probe portion of the catheter is manufactured with sufficient rigidity to avoid collapsing upon itself while being advanced through the nucleus pulposus and navigated around the inner wall of the annulus fibrosus. The probe portion, however, can have insufficient rigidity to puncture the annulus fibrosus under the same force used to advance the catheter through the nucleus pulposus and around the inner wall of the annulus fibrosus. Absolute penetration ability will vary with sharpness and stiffness of the tip of the catheter, but in all cases a catheter of the present invention will optionally advance more readily through the nucleus pulposus than through the annulus fibrosus.

In optional embodiments, the probe section of the catheter further has differential bending ability in two orthogonal directions at right angles to the longitudinal axis. This optionally causes the catheter to bend along a desired plane (instead of at random). Also when a torsional (twisting) force is applied to the proximal end of the catheter to optionally re-orient the distal end of the catheter, controlled advancement of the catheter in the desired plane can be provided.

A further component of the catheter optionally is a functional element located in the probe section for diagnosis or for adding energy and adding and/or removing material at the selected location of the disc where the annular tear is to be treated. The apparatus optionally allows the functional element to be controllably guided by manipulation of the proximal end of the catheter into a selected location for localized treatment of the annular fissure.

The optional method embodiment of the invention, which optionally involves manipulating disc tissue at the annular fissure, is easily carried out with an apparatus of the invention. An introducer is provided that is located in a patient's body so that its proximal end is external to the body and the distal opening of its lumen is internal to the body and (1) internal to the annulus fibrosus or (2) adjacent to an annular opening leading to the nucleus pulposus, such as an annular tear or trocar puncture that communicates with the nucleus pulposus. The catheter is optionally then slid into position in and through the introducer lumen so that the functional elements in the catheter are positioned at the selected location of the disc by advancing or retracting the catheter or probe in the introducer lumen and optionally twisting the proximal end of the catheter to precisely navigate the catheter. By selection of the rigidity of the catheter and by making it sufficiently blunt to not penetrate the annulus fibrosus, and by selection of the flexibility in one plane versus the orthogonal plane, the distal portion of the catheter optionally will curve along the inner wall of the annulus fibrosus as it is navigated and is selectively guided to an annular tear at selected location(s) in the disc. Energy and spinal disk herniation repositioning is optionally applied and/or material is added or removed at the selected location of the disc via the functional elements.

Each of the elements of the apparatus and method will now be described in more detail. However, a brief description of disc anatomy is provided first, as sizes and orientation of structural elements of the apparatus and operations of the method can be better understood in some cases by reference to disc anatomy.

A Non Limiting Exemplary Surgical Site

The annulus fibrosus is comprised primarily of tough fibrous material, while the nucleus pulposus is comprised primarily of an amorphous colloidal gel. There is a transition zone between the annulus fibrosus and the nucleus pulposus made of both fibrous-like material and amorphous colloidal gel. The border between the annulus fibrosus and the nucleus pulposus becomes more difficult to distinguish as a patient ages, due to degenerative changes. This process may begin as early as 30 years of age. For purposes of this specification, the inner wall of the annulus fibrosus can include the young wall comprised primarily of fibrous material as well as the transition zone which includes both fibrous material and amorphous colloidal gels (hereafter collectively referred to as the "inner wall of the annulus fibrosus"). Functionally, that location at which there is an increase in resistance to catheter penetration and which is sufficient to cause bending of the distal portion of the catheter into a radius less than that of the internal wall of the annulus fibrosus is considered to be the "inner wall of the annulus fibrosus."

As with any medical instrument and method, not all patients can be treated, especially when their disease or injury is too severe. There is a medical gradation of degenerative disc disease (stages 1-5). See, for example, Adams et al., "The Stages of Disc Degeneration as Revealed by Discograms," J. Bone and Joint Surgery, 68, 36-41 (1986), entirely incorporated herein by reference. As these grades are commonly understood, the methods of instrument navigation described herein can distinguish between the nucleus and the annulus in degenerative disease of grades, such as in discs in stages 3 and 4, optionally up to 5, and optionally as early as stages 1 and 2, but which are often asymptomatic in most patients, and stage 5 may require disc removal and fusion.

Some of the following discussion refers to motion of the catheter inside the disc by use of the terms "disc plane," "oblique plane" and "cephalo-caudal plane." These specific terms refer to orientations of the catheter within the intervertebral disc.

Referring to FIGS. 1-8, when the side needle (2) of the electrode is deployed, the probe and the side needle would form an "r" shape, allowing physicians to use mechanical force to push annulus and diseased tissues away from the nerves.

The side needle (2) is also equipped with a thermocouple, allowing physicians to monitor and control the temperature when performing radiofrequency ablation procedures.

The electrode itself has the following major components: Probe (1); Side needle (2); Operation handle (3); Push button (4); Injection nozzle (5); Electric cable (8); Power plug (7).

In this electrode, the probe (1) and the side needle (2) are both made of metal tubes. The side needle (2) is connected to the proximal end (B) of the sheath (10) through the probe (1); the sheath (10) is connected to the push button (4) through a connection piece (12), thus when the physician moves the push button (4), the side needle (2) could be either deployed or retrieved.

The side needle (2) is also equipped with a thermocouple (13) at the tip position. The thermocouple (13) is connected to the inner chamber of the side needle (2), the electrical cable (8) and the power plug (7), allowing physicians to monitor and control the temperature when performing radiofrequency ablation procedure.

In addition, medicines could be injected through the injection nozzle (5), injection tube (14), injection sheath (6) and the inner chamber of the probe (1) to reach the distal end of the probe as well the side holes (D). Similarly, ozone or collagenase could be injected through the same mechanism.

Figure Descriptions of Optional Non Limiting Embodiments

FIG. 1: shows a schematic of an outside view of the electrode and two or more of the following major components: Probe (1); Side needle (2); Operation handle (3); Push button (4); Injection nozzle (5); Electric cable (8); and Power plug (7). The side needle (2) can optionally be located at the same side as the push button (4). The probe and the side needle can optionally form an "r" shape, making it easier for physicians to puncture through the tissues.

Figure 2:
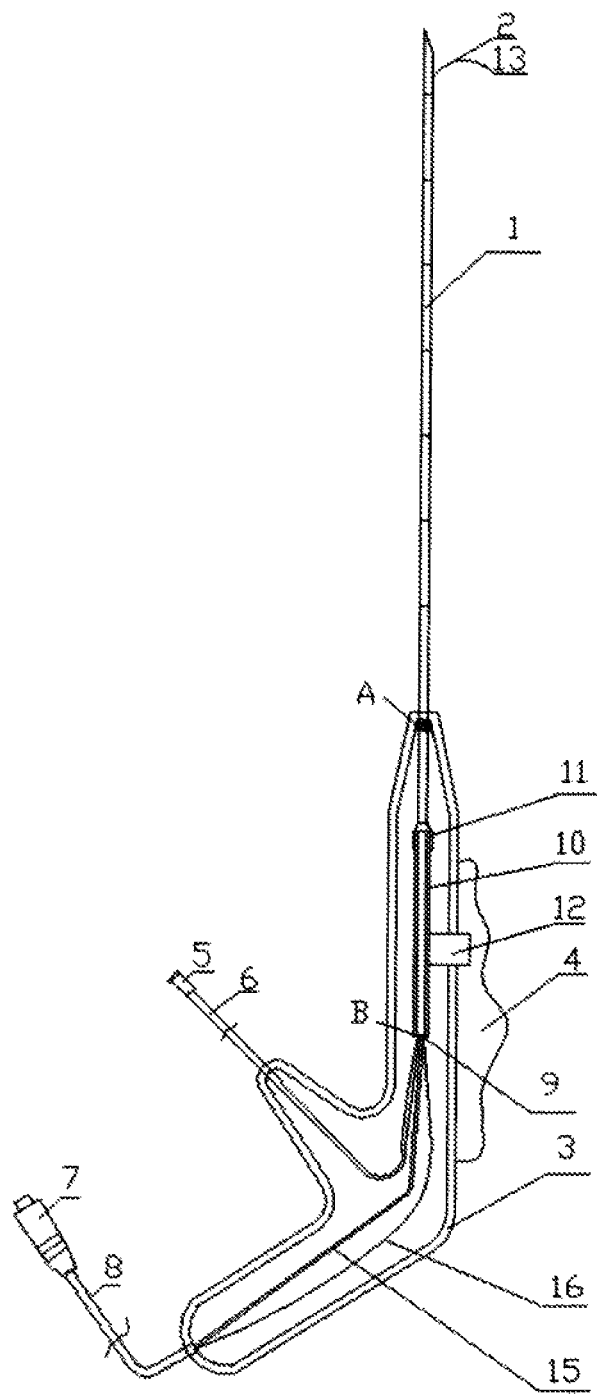
FIG. 2 is a cut away view of a schematic picture of a non-limiting example of a device of the invention.

FIG. 2: shows an optional inside view of the electrode, e.g., but not limited to, wherein the probe (1) and operation handle (3) can be attached or associated, by mechanical or other connection (e.g., but not limited to attached or glued together at point A). The sheath (10) can optionally be a tube outside the proximal end of the probe (1). The distal end of the sheath (10) can optionally have a seal pipe (11) to seal the space between the operation handle (3) and the probe (1). The proximal end of the sheath (10) and the proximal end of the side needle (2) can be attached or associated, by mechanical or other connection (e.g., but not limited to attached or glued together. With the protection of the seal pipe (11), the sheath (10) and the probe (1) can optionally slide smoothly without or substantially reduced leakage problems. The sheath (10) can optionally be connected to the push button (4) through a connection piece (12), thus when the physician moves the push button (4), the side needle (2) can optionally be either deployed or retrieved.

Figure 3:
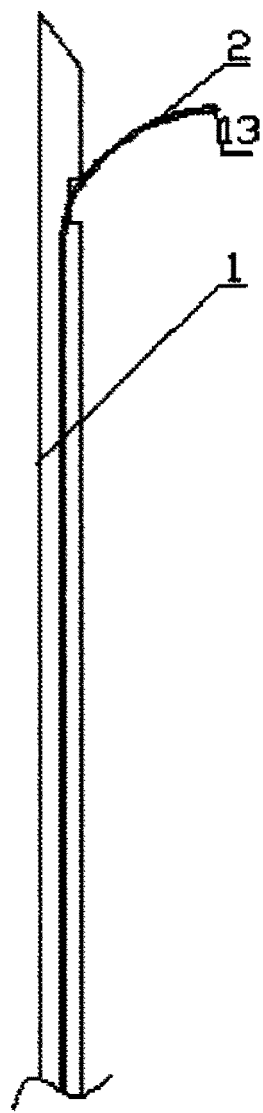
FIG. 3: is a schematic picture of a non-limiting example of a device of the invention showing a probe's distal end and a side needle.

FIG. 3: shows optional probe's distal end and side needle: The distal end of the probe (1) can optionally have a sloped shape. Underneath the slope optionally is a side hole: the hole is optionally either rectangular or oval shaped, allowing side needle (2) to be deployed or retrieved.

Figure 4:
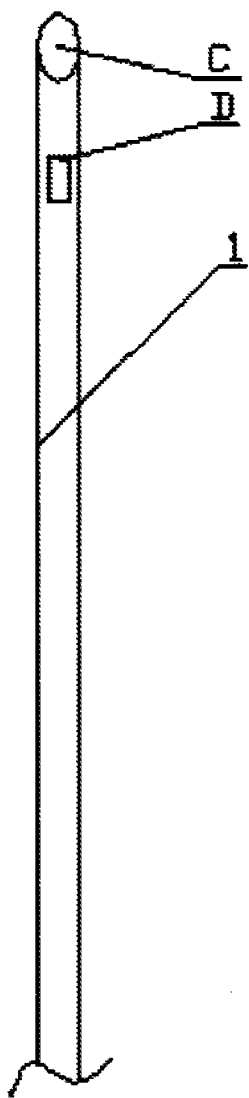
FIG. 4: is a schematic picture of a non-limiting example of a device of the invention showing a distal end slope tip and side hole

FIG. 4 shows the distal end slope and side hole. The tip of the probe (1) optionally has a sloped shape (point C). A rectangular-shaped hole optionally sits underneath the slope.

Figure 5:
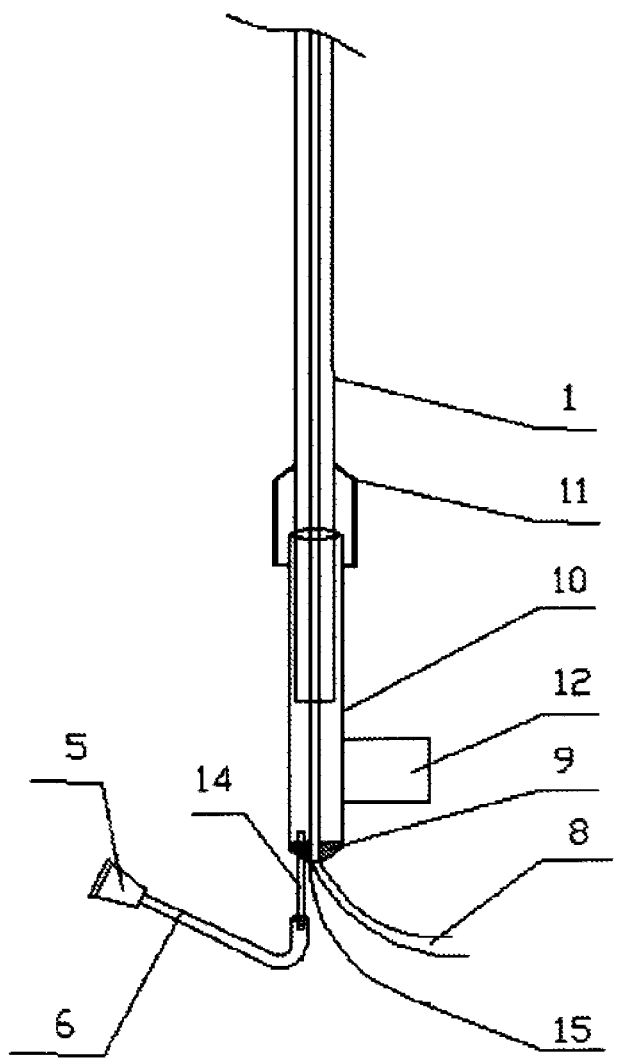
FIG. 5: is a schematic picture of a non-limiting example of a device of the invention showing a proximal end and sheath

FIG. 5 shows an optional proximal end and sheath. The sheath (10) optionally is a tube outside the proximal end of the probe (1). The distal end of the sheath (10) optionally has a seal pipe (11) to seal the space between the operation handle (3) and the probe (1). The proximal end of the sheath (10) and the proximal end of the side needle (2) can be attached or associated, by mechanical or other connection (e.g., but not limited to attached or glued together, e.g., optionally using a sealant (9).

Figure 6:
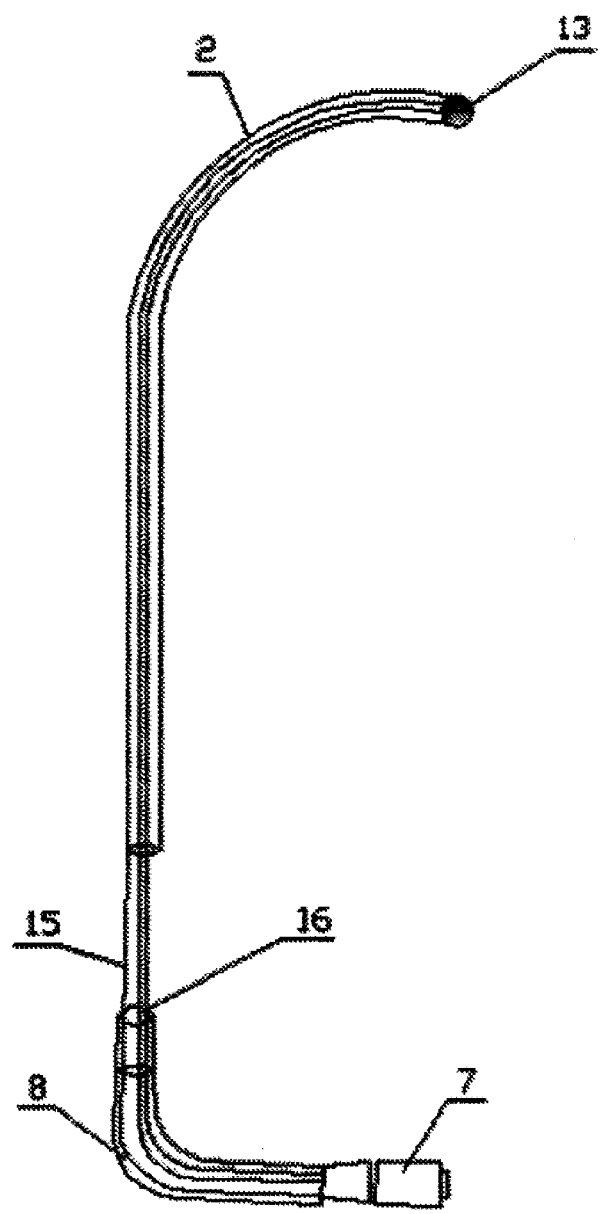
FIG. 6: is a schematic picture of a non-limiting example of a device of the invention showing a electrical connections

FIG. 6 shows optional electrical connections. The side needle (2) is optionally equipped with a thermocouple (13) at the tip position. The thermocouple (13) optionally is connected to the inner chamber of the side needle (2), optionally through a thermocouple cable (15). The thermocouple cable (15) is optionally also connected to the electrical cable (8) and the power plug (7). There is optionally a radiofrequency cable (16) between the proximal end of the side needle (2) and the power plug (7).

Figure 7:
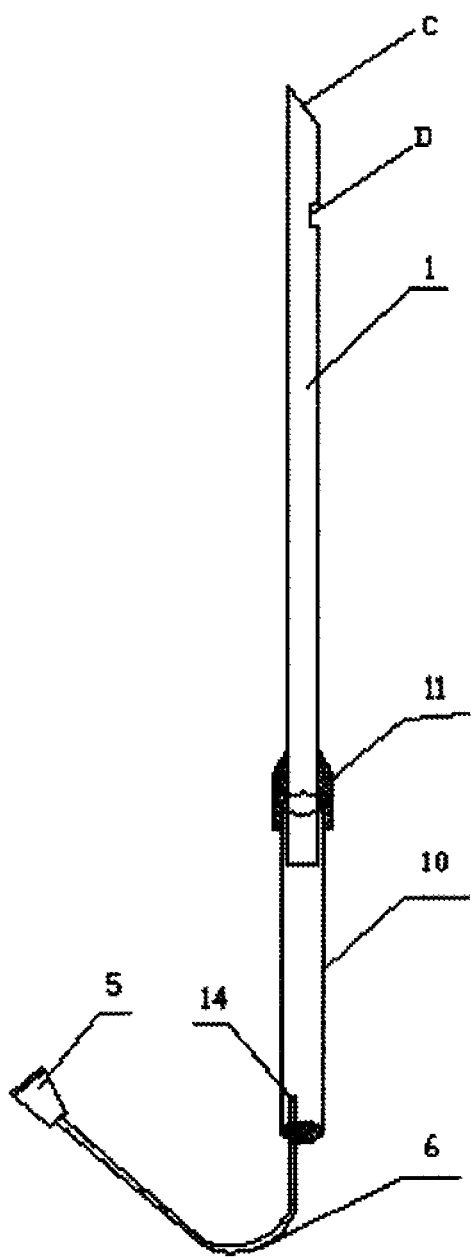
FIG. 7: is a schematic picture of a non-limiting example of a device of the invention showing medicine injection channels.

FIG. 7 shows optional medicine injection channels. Medicines (e.g. ozone and collagenase) optionally are injected through the injection nozzle (5), injection sheath (6) and the inner chamber of the probe (1) to reach the distal end of the probe as well the side holes, and to enter the diseased or other tissues for therapy or diagnosis.

Figure 8:
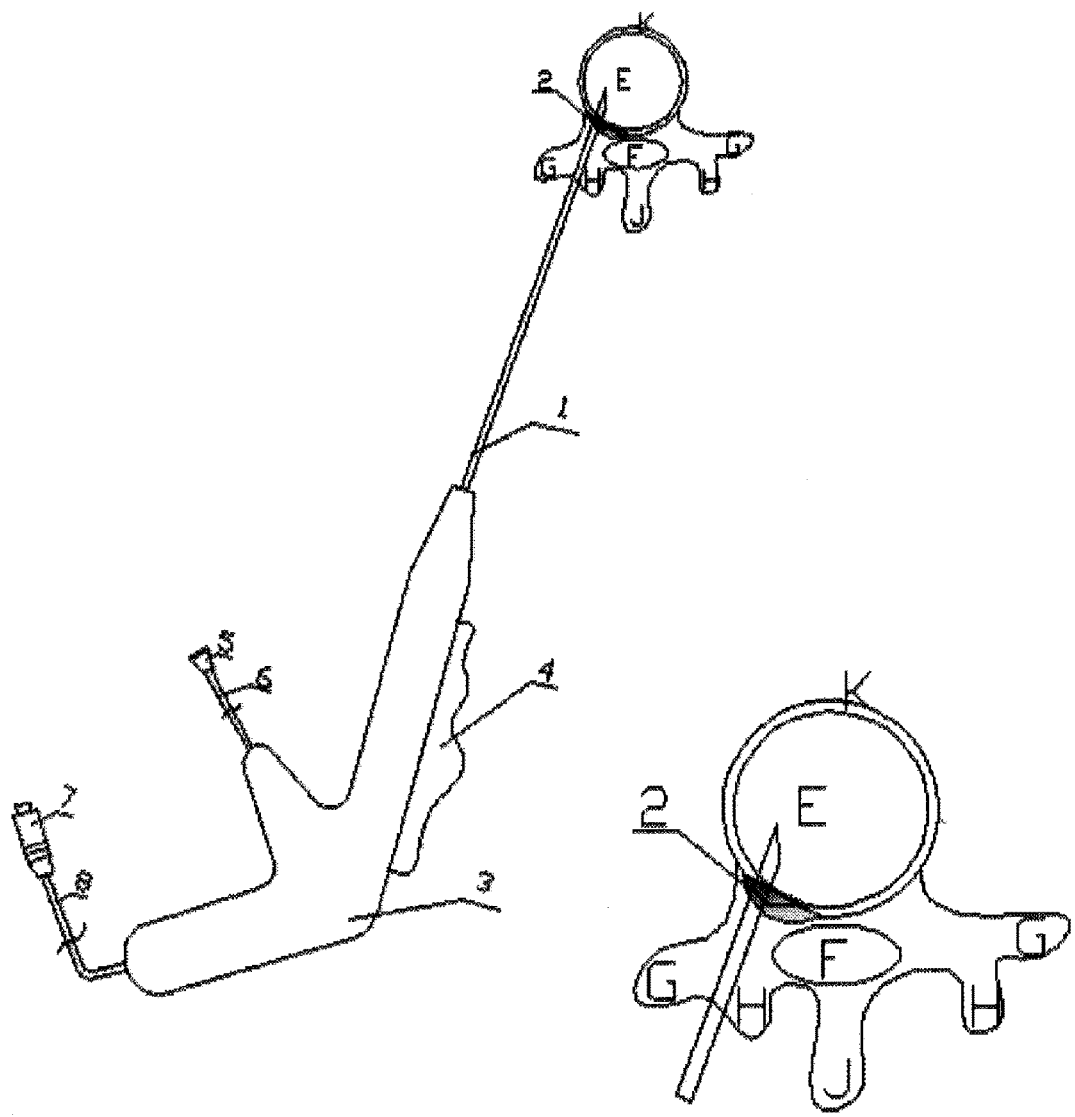
FIG. 8: is a schematic picture of a non-limiting example of a device of the invention showing Spinal Disk Herniation Treatment.

FIG. 8 shows optional Spinal Disk Herniation Treatment. Optionally under the guidance of imaging devices (e.g. CT), physicians can optionally use the electrode's probe to puncture the body. After the needle reaches the injured part, the physician optionally deploys the side needle in order to reposition the spinal disk herniation. Later the physician optionally performs radiofrequency ablation treatment as well as optional medicine/ozone therapy with the device.

In a non limiting optional embodiment of a catheter of the invention as it would appear inserted into the lumen of an introducer. The catheter includes handle, stem, probe section and a tip. The handle at the proximal end of the catheter is coupled via the stem to the probe section, which is located proximate the distal end of the device. At the terminus of the probe, i.e., the distal end of the device, is the tip. The tip may be axially displaced from the probe section. Functional elements for delivery or energy or material to or from the site in combination with a spinal disk herniation repositioning element can be placed within the probe. These can, via connections within the probe, stem and handle, be coupled to either an RF energy delivery device 1 and the repositioning needle 2 or a material transfer device. Therefore no limitation should be placed on the types of energy, spinal disk herniation repositioning, force, or material transporting elements present in the catheter. These are merely some of the possible alternative functional elements that can be included in the probe portion of the catheter. The flexible, movable catheter is at least partially positionable in the introducer lumen, to bring the probe section, which is designed to be the portion of the catheter that will be pushed out of the introducer lumen and into the nucleus pulposus and into the selected location(s) with regard to the annular tear.

Non limiting optional embodiments can include one or more of an apparatus for treating herniated spinal discs comprising one or more of a radiofrequency (RF) ablation electrode with repositioning features, the ablation electrode comprising: a probe electrode (1); a side needle spinal disk herniation repositioning electrode (2); a handle (3); a control button (4); an injection nozzle (5); a power cable (8); and a power plug (7) connecting to an RF generator; wherein the probe (1) has a sloped shape and a side hole;
optionally wherein the hole is rectangular or oval shaped, allowing the side needle to be deployed or retrieved;
optionally wherein the probe (1) and the side needle (2) are both made of metal tubes; the side needle (2) is connected to the proximal end of the sheath (10) through the probe (1); the sheath (10) is connected to the push button (4) through a connection piece (12), such that the push button (4) controls the side needle (2) for deployment or retrieval;
optionally wherein the side needle (2) further comprises a thermocouple (13) at the tip position connected to the inner chamber of the side needle (2), the electrical cable (8) and the power plug (7), providing monitoring and control of the temperature when performing radiofrequency ablation procedures;
optionally wherein medicines, ozone or collagenase, are injectable through the injection nozzle (5), injection sheath (6) and the inner chamber of the probe (1) to reach the distal end of the probe as well the side holes.

FIG. 2 shows a longitudinal cross-section of the device comprising a probe electrode (1); a side needle spinal disk herniation repositioning electrode (2); a handle (3); a control button (4); an injection nozzle (5); a power cable (8); and a power plug (7) connecting to an RF generator; wherein the probe electrode (1) has a sloped shape and a side hole.

For one embodiment suitable for intervertebral discs, the outer diameter of catheter is optionally in the range of 0.2 to 1.5 mm, the total length of catheter (including the portion inside the introducer) is in the range of 10 to 60 cm, and the length of introducer is in the range of 5 to 50 cm. For one optional embodiment, the catheter has a diameter of 1 mm, an overall length of 30 cm, and an introduced length of 15 cm (for the probe section). With an instrument of this size, a physician can insert the catheter for a distance sufficient to reach selected location(s) in the nucleus of a human intervertebral disc.

Any device in which bending of the tip of a catheter of the invention is at least partially controlled by the physician is "actively steerable." A mandrel may facilitate the active steering of a catheter.

Active Steering of Catheter

A guiding mandrel can be included both to add rigidity to the catheter and to inhibit movement of probe section of the catheter along an inferior axis while allowing it along a superior axis while positioned and aligned in the disc plane of a nucleus pulposus. This aids the functions of preventing undesired contact with a vertebra and facilitating navigation. The mandrel can be flattened to encourage bending in a plane (the "plane of the bend") orthogonal to the "flat" side of the mandrel. "Flat" here is a relative term, as the mandrel can have a D-shaped cross-section, or even an oval or other cross-sectional shape without a planar face on any part of the structure. Regardless of the exact configuration, bending will preferentially occur in the plane formed by the principal longitudinal axis of the mandrel and a line connecting the opposite sides of the shortest cross-sectional dimension of the mandrel (the "thin" dimension). To provide sufficient resistance to the catheter bending out of the desired plane while encouraging bending in the desired plane, the minimum ratio is 1.25:1 ("thickest" to "thinnest" cross-sectional dimensions along at least a portion of the probe section). The maximum ratio is 20:1, with the preferred ratio being between 1.5:1 and 16:3, more preferably between 2:1 and 3.5:1. These ratios are for a solid mandrel and apply to any material, as deflection under stress for uniform solids is inversely proportional to the thickness of the solid in the direction (dimension) in which bending is taking place. For other types of mandrels (e.g., hollow or non-uniform materials), selection of dimensions and/or materials that provide the same relative bending motions under stress are preferred.

A catheter of the present invention is designed with sufficient torsional strength (resistance to twisting) to prevent undesired directional movement of the catheter. Mandrels formed from materials having tensile strengths in the range set forth in the examples of this specification provide a portion of the desired torsional strength. Other materials can be substituted so long as they provide the operational functions described in the examples and desired operating parameters.

While the mandrel can provide a significant portion of the column strength, selective flexibility, and torsional strength of a catheter, other structural elements of the catheter also contribute to these characteristics. Accordingly, it must be kept in mind that it is the characteristics of the overall catheter that determine suitability of a particular catheter for use in the methods of the invention. Similarly, components inside the catheter, such as a heating element or potting compound, can be used to strengthen the catheter or provide directional flexibility at the locations of these elements along the catheter.

It is not necessary that the guiding mandrel be flattened along its entire length. Different mandrels can be designed for different sized discs, both because of variations in disc sizes from individual to individual and because of variations in size from disc to disc in one patient. The bendable portion of the mandrel is preferably sufficient to allow probe section of the catheter to navigate at least partially around the circumference of the inner wall of the annulus fibrosus (so that the operational functions of the catheter can be carried out at desired location(s) along the inner wall of the annulus fibrosus). Shorter bendable sections are acceptable for specialized instruments. In most cases, a flattened distal portion of the mandrel of at least 10 mm, preferably 25 mm, is satisfactory. The flattened portion can extend as much as the entire length of the mandrel, with some embodiments being flattened for less than 15 cm, in other cases for less than 10 cm, of the distal end of the guide mandrel.

In optional embodiments, the guide mandrel or other differential bending control element is maintained in a readily determinable orientation by a control element located at the proximal end of the catheter. The orientation of the direction of bending and its amount can be readily observed and controlled by the physician. One possible control element is simply a portion of the mandrel that extends out of the proximal end of the introducer and can be grasped by the physician, with a shape being provided that enables the physician to determine the orientation of the distal portion by orientation of the portion in the hand. For example, a flattened shape can be provided that mimics the shape at the distal end (optionally made larger to allow better control in the gloved hand of the physician). More complex proximal control elements capable of grasping the proximal end of the mandrel or other bending control element can be used if desired, including but not limited to electronic, mechanical, and hydraulic controls for actuation by the physician.

The guide mandrel can also provide the function of differential flexibility by varying the thickness in one or more dimensions (for example, the "thin" dimension, the "thick" dimension, or both) along the length of the mandrel. A guide mandrel that tapers (becomes gradually thinner) toward the distal tip of the mandrel will be more flexible and easier to bend at the tip than it is at other locations along the mandrel. A guide mandrel that has a thicker or more rounded tip than more proximal portions of the mandrel will resist bending at the tip but aid bending at more proximal locations. Thickening (or thinning) can also occur in other locations along the mandrel. Control of the direction of bending can be accomplished by making the mandrel more round, i.e., closer to having 1:1 diameter ratios; flatter in different sections of the mandrel; or by varying the absolute dimensions (increasing or decreasing the diameter). Such control over flexibility allows instruments to be designed that minimize bending in some desired locations (such as the location of a connector of an electrical element to avoid disruption of the connection) while encouraging bending in other locations (e.g., between sensitive functional elements). In this manner, a catheter that is uniformly flexible along its entire length, is variably flexible along its entire length, or has alternating more flexible and less flexible segment(s), is readily obtained simply by manufacturing the guide mandrel with appropriate thickness at different distances and in different orientations along the length of the mandrel. Such a catheter will have two or more different radii of curvature in different segments of the catheter under the same bending force.

In some preferred embodiments, the most distal 3 to 40 mm of a guide mandrel is thinner relative to central portions of the probe section to provide greater flexibility, with the proximal 10 to 40 mm of the probe section being thicker and less flexible to add column strength and facilitate navigation.

The actual dimensions of the guide mandrel will vary with the stiffness and tensile strength of the material used to form the mandrel. In most cases the mandrel will be formed from a metal (elemental or an alloy) or plastic that will be selected so that the resulting catheter will have characteristics of stiffness and bending that fall within the stated limits. Additional examples of ways to vary the stiffness and tensile strength include transverse breaks in a material, advance of the material so that it "doubles up," additional layers of the same or different material, tensioning or relaxing tension on the catheter, and applying electricity to a memory metal.

Multi-Dimensional Probe Deployment

Catheters which are actively steerable, may include additionally the capability of deploying into planar substantially two dimensional shapes or three dimensional shapes which conform to the surgical site. These multi-dimensional deployment capabilities, reduce operating time, improve operational accuracy and increase the utility of surgical intervention.

Linear to Arcuate Transition of Probe

Optional embodiments can include apparatus and methods for transitioning a probe from a linear to a multi-dimensional shape. The transition of the probe from a linear to an arcuate shape may be brought about by any of a group of activation elements including, but not limited to, the following.

In an embodiment of the invention the probe may include a resilient material, e.g. a heat treated metal or spring metal, which will assume a linear shape only by virtue of the guiding force of the lumen portion of the introducer and will resume its original arcuate shape, upon introduction to the surgical site and by extension beyond the confines of the introducer. The resilient spring-like material is arcuate in the absence of external stress but, under selected stress conditions (for example, while the catheter is inside the introducer), is linear. Such a biased distal portion can be manufactured from either spring metal or superelastic memory material (such as Tinel® nickel-titanium alloy, Raychem Corp., Menlo Park Calif.). The introducer (at least in the case of a spring-like material for forming the catheter) is sufficiently strong to resist the bending action of the bent tip and maintain the biased distal portion in alignment as it passes through the introducer. Compared to unbiased catheters, a catheter with a biased probe encourages advancement of the probe substantially in the direction of the bend relative to other lateral directions. Biasing the catheter tip also further decreases likelihood that the tip will be forced through the annulus fibrosus under the pressure used to advance the catheter. In those embodiments utilizing a resilient material as an introducer in combination with the resilient material is necessary in order to introduce the probe in a linear or lay flat configuration to the surgical site.

Although an introducer may also be used with any of the following activation elements it is not necessary to bring about the transition from a linear to an arcuate shape.

In another embodiment of the invention, the probe may include at least two materials with a different coefficient of thermal expansion joined to one another along their length, such that at one temperature, e.g., room temperature, they are linear while at an elevated temperature, the differential expansion of one with respect to the other induces an arcuate bending of both. Bi-metallic strips such as copper and steel might serve this function. Any other two metals with different coefficients of expansion could be substituted for copper and steel. The greater the differential of the coefficients of expansion between the two metals the smaller the radius(s) of the arcuate shape formed thereby at any given temperature differential. Other materials besides metals with different coefficients of expansion could also be used. The temperature differential of the at least two materials at room temperature and at the surgical site may be increased by energy delivered to the probe, e.g., RF or resistive heating. Alternately, electrical power may be applied directly to one or both of the at least two materials provided they are electrically resistive such that the application of power will result in heat generation.

In another embodiment of the invention the arcuate shape may be brought about by use of materials with temperature dependent shape memory such as the metal alloy Nitinol. The probe is fabricated to be linear at room temperature and arcuate at the temperature of the surgical site. The temperature differential of the Nitinol at room temperature and at the surgical site may be increased by energy delivered to the probe, e.g. RF or resistive heating. Alternately the electrical power may be directly applied directly to the Nitinol which is itself a resistive element.

In another embodiment of the invention, the arcuate shape may be induced using electrical activated expansion and contraction of materials within the probe. Piezoelectric crystals positioned on either the exterior or interior radius of the arc may be used in this manner to respectively expand or contract against a surface of a mandrel within the probe, to induce an arcuate shape.

In still another embodiment of the invention the alteration of shape from linear to arcuate may be produced by mechanical means such as the combination of a draw wire and mandrel, coupled at the tip of the device and extending the length of the catheter, such that tension of the draw wire induces tension on a side of the mandrel inducing it to assume an arcuate shape. Numerous combinations of material and energy, either thermal or electrical can be used to create a deformable tip.

An advantageous feature of all the probes set forth in the current invention is that their shape can be configured to conform to the interior shape of the surgical site to which they are introduced, thus placing functional elements on the probe into proximity with all portions of the surgical site without the need for a point-by-point navigation of the probe tip about the surgical site.

Functional Elements

Since a purpose of the inventive catheter is to repair tears or fissures in a disc by operation of the instrument at the tear location adjacent to or inside the disc, a functional element is provided in or on the catheter to carry out that purpose.

Non-limiting examples of functional elements include any element capable of aiding diagnosis, delivering energy, or delivering or removing a material from a location adjacent the element's location in the catheter, such as an opening in the catheter for delivery of a fluid (e.g., dissolved collagen to seal the fissure) or for suction, a thermal energy delivery device (heat source), a mechanical grasping tool for removing or depositing a solid, a cutting tool (which includes all similar operations, such as puncturing), a sensor for measurement of a function (such as electrical resistance, temperature, or mechanical strength), or a functional element having a combination of these functions.

The functional element can be at varied locations in the probe portion of the catheter, depending on its intended use. Multiple functional elements can be present, such as multiple functional elements of different types (e.g., a heat source and a temperature sensor) or multiple functional elements of the same type (e.g., multiple heat sources spaced along the probe portion).

One of the possible functional elements present on probe section is a thermal energy delivery device. A variety of different types of thermal energy can be delivered including but not limited to resistive heat, radio frequency (RF), coherent and incoherent light, microwave, ultrasound and liquid thermal jet energies. In one embodiment, thermal energy delivery device is positioned proximal to the distal portion of probe section so that there is no substantial delivery of energy at the distal portion, which can then perform other functions without being constrained by being required to provide energy (or resist the resulting heat).

The energy directing device is configured to limit thermal and/or electromagnetic energy delivery to a selected site of the disc and to leave other sections of the disc substantially unaffected. The energy can be directed to the walls of the fissure to cauterize granulation tissue and to shrink the collagen component of the annulus, while the nucleus is shielded from excess heat.

In another embodiment, sufficient energy is delivered to the intervertebral disc to heat and shrink the collagen component of the annulus but not ablate tissue adjacent to catheter. With a resistive heating device, the amount of thermal energy delivered to the tissue is a function of (i) the amount of current passing through the heating element, (ii) the length, shape, and/or size of the heating element, (iii) the resistive properties of the heating element, (iv) the gauge of the heating element, and (v) the use of cooling fluid to control temperature. All of these factors can be varied individually or in combination to provide the desired level of heat. Energy delivery device associated with the heating element may be battery based. The catheters can be sterilized and may be disposable.

The lumen may be configured to transport a variety of different mediums including but not limited to electrolytic solutions (such as normal saline), contrast media (such as Conray meglumine iothalamate), pharmaceutical agents, disinfectants, filling or binding materials such as collagens or cements, chemonucleolytic agents and the like, from the material delivery/removal device to a desired location within the interior of a disc (i.e., the fissure). Further, the lumen can be used to remove nucleus material or excess liquid or gas (naturally present, present as the result of a liquefying operation, or present because of prior introduction) from the interior of a disc. When used to transport a fluid for irrigation of the location within the disc where some action is taking place (such as ablation, which generates waste materials), the lumen is sometimes referred to as an irrigation lumen. The lumen can be coupled to the material delivery/removal device through the catheter. In addition to or in substitution for the cutting blade, other instruments can be delivered through the lumen including but not limited to: graspers, drill and biopsy needle.

All publications, patent applications, and issued patents mentioned in this application are hereby incorporated herein by reference in their entirety to the same extent as if each individual publication, application, or patent was specifically and individually indicated to be incorporated in its entirety by reference.

All the disclosed embodiments of the invention described herein can be realized and practiced without undue experimentation. Although the best mode of carrying out the invention contemplated by the inventors is disclosed above, practice of the present invention is not limited thereto. Accordingly, it will be appreciated by those skilled in the art that the invention may be practiced otherwise than as specifically described herein.

For example, the individual components need not be formed in the disclosed shapes, or assembled in the disclosed configuration, but could be provided in virtually any shape, and assembled in virtually any configuration. Further, the individual components need not be fabricated from the disclosed materials, but could be fabricated from virtually any suitable materials. Furthermore, all the disclosed elements and features of each disclosed embodiment can be combined with, or substituted for, the disclosed elements and features of every other disclosed embodiment except where such elements or features are mutually exclusive.

It will be manifest that various additions, modifications and rearrangements of the features of the present invention may be made without deviating from the spirit and scope of the underlying inventive concept. It is intended that the scope of the invention as defined by the appended claims and their equivalents cover all such additions, modifications, and rearrangements. The appended claims are not to be interpreted as including means-plus-function limitations, unless such a limitation is explicitly recited in a given claim using the phrase "means for." Expedient embodiments of the invention are differentiated by the appended subclaims.

What is claimed is:

1. A method for using an apparatus configured for treating a herniated spinal disc in the body of a patient using a single side needle electrode (2) that provides the combination of all of herniated tissue repositioning, temperature sensing, and radiofrequency ablation, the method comprising:
   (a) providing the apparatus comprising:
      a probe (1) comprising an inner chamber and, at distal end (C), a sloped shaped tip and a side hole (D);
      the single side needle electrode (2) deployable through the probe inner chamber and said side hole (D); and the single side needle electrode (2) comprising a thermocouple (13) at a distal end, wherein the single side needle electrode (2) is provided to operate through the side hold (D) of the probe (1) as a single needle;
      a handle (3);
      a control button (4);
      an injection nozzle (5);
      an injection sheath (6);
      a power cable (8);
      a RF generator; a power plug (7) configured to connect to the RF generator,
   (b) manipulating the handle (3) of the apparatus to move the distal end (C) of the probe (1) to puncture the body of the patient for placement of the distal end (C) of the probe (1) adjacent to the herniated disc;
   (c) deploying the distal end of the single side needle electrode (2) comprising the thermocouple (13) through the side hole (D) of the probe (1) to reposition herniated tissue of the herniated disc away from herniated areas of the herniated disc to provide repositioned herniated tissue to reduce oppression of nerves adjacent to the herniated tissue to relieve pain; and
   (d) performing radiofrequency ablation (RFA) treatment of the repositioned herniated tissue of the herniated disc using the distal end of the single side needle electrode (2) comprising the thermocouple (13) operably connected to the power cable (8) and the power plug (7), which are configured to be operably connected to the RF generator, to reduce the size of the herniated tissue to reduce oppression of nerves adjacent to the herniated tissue to relieve pain;
   (e) monitoring and controlling of the temperature of the distal end of the single side needle electrode (2) via said thermocouple (13) during said step of performing said radiofrequency ablation treatment;
   (f) applying thermal energy into collagen in the area of an annular fissure in the herniated disc using the thermocouple (13) at the distal end of the single needle electrode (2) to strengthen the annulus and to fuse collagen to the sides of the fissure;
   (g) injecting medicines, ozone or collagenase through the injection nozzle (5), the injection sheath (6), the inner chamber of the probe (1), and the side hole (D) of the probe (1) to treat the herniated areas of the herniated disc;
   wherein the herniated tissue repositioning, radiofrequency ablation, and temperature monitoring and controlling steps use the same side needle electrode (2);
   wherein the side hole (D) is rectangular or oval shaped, and is configured to allow the single side needle electrode (2) to be deployed or retracted during said performing and monitoring and controlling steps;
   wherein the probe (1) and the single side needle electrode (2) are both made of metal tubes; the single side needle electrode (2) is connected to a proximal end (B) of a sheath (10) through the probe (1); and the sheath (10) is connected to the control button (4) through a connection piece (12), such that the control button (4) controls the single side needle electrode (2) for deployment or retraction through the side hole (D); and
   wherein the metal tubes are provided as concentric shafts for said injecting said medicines, ozone or collagenase in step (g).

2. An apparatus configured treating a herniated spinal disc in the body of a patient using a single side needle electrode (2) that provides the combination of all of herniated tissue repositioning, temperature sensing, and radiofrequency ablation,
   the apparatus comprising:
      a probe (1) comprising an inner chamber and, at distal end (C), a sloped shaped tip and a side hole (D);
      the single side needle electrode (2) comprising a thermocouple (13) at a distal end, wherein the single side needle electrode (2) is configured to: (i) be deployable through the probe inner chamber and the side hole (D); and (ii) operate through the side hold (D) of the probe (1) as a single needle;
      a handle (3);
      a control button (4);
      an injection nozzle (5);

an injection sheath (6);
a power cable (8);
a RF generator, a power plug (7) configured to connect to the RF generator,
wherein the handle (3) of the apparatus is configured to manipulate the distal end (C) of the probe (1) to puncture the body of the patient for placement of the distal end (C) of the probe (1) adjacent to the herniated disc;
wherein the distal end of the single side needle electrode (2) comprising the thermocouple (13) is configured to be deployed through the side hole (D) of the probe (1) to reposition herniated tissue of the herniated disc away from herniated areas of the herniated disc to provide repositioned herniated tissue to reduce oppression of nerves adjacent to the herniated tissue to relieve pain; and
wherein the distal end of the single side needle electrode (2) comprising the thermocouple (13), operably connected to the power cable (8); the power plug (7); and the RF generator, is configured to:
 (a) perform radiofrequency ablation (RFA) treatment of the repositioned herniated tissue of the herniated disc;
 (b) reduce the size of the herniated tissue to reduce oppression of nerves adjacent to the herniated tissue to relieve pain;
wherein the thermocouple (13) is configured to monitor and control the temperature of the distal end of the single side needle electrode (2);
wherein the thermocouple (13) at the distal end of the single needle electrode (2) is configured to apply thermal energy into collagen in the area of an annular fissure in the herniated disc to strengthen the annulus and to fuse collagen to the sides of the fissure;
wherein the probe (1) is configured to inject medicines, ozone or collagenase through the injection nozzle (5), the injection sheath (6), the inner chamber of the probe (1), and the side hole (D) of the probe (1) to treat the herniated areas of the herniated disc;
wherein the side hole (D) is rectangular or oval shaped, and is configured to allow the single side needle electrode (2) to be deployed or retracted during the repositioning, radio frequency ablation, manipulation, deployment, monitoring and controlling;
wherein the probe (1) and the single side needle electrode (2) are both made of metal tubes; the single side needle electrode (2) is connected to a proximal end (B) of a sheath (10) through the probe (1); and the sheath (10) is connected to the control button (4) through a connection piece (12), such that the control button (4) controls the single side needle electrode (2) for deployment or retraction through the side hole (D); and
wherein the metal tubes are provided as concentric shafts for said injecting said medicines, ozone or collagenase.

\* \* \* \* \*